(12) United States Patent
Temple et al.

(10) Patent No.: US 9,314,330 B2
(45) Date of Patent: Apr. 19, 2016

(54) FAN FOLDED FASCIA LATA FOR CRUCIATE LIGAMENT SUBSTITUTION AND METHOD AND APPARATUS FOR MAKING THE SAME

(75) Inventors: H. Thomas Temple, Miami, FL (US); Theodore I. Malinin, Key Biscayne, FL (US); Siu Tung Wu, Miami, FL (US)

(73) Assignee: Vivex Biomedical, Inc., Marietta, GA (US)

( * ) Notice: Subject to any disclaimer, the term of this patent is extended or adjusted under 35 U.S.C. 154(b) by 505 days.

(21) Appl. No.: 13/520,734

(22) PCT Filed: Jan. 10, 2011

(86) PCT No.: PCT/US2011/020650
§ 371 (c)(1),
(2), (4) Date: Jul. 5, 2012

(87) PCT Pub. No.: WO2011/087976
PCT Pub. Date: Jul. 21, 2011

(65) Prior Publication Data
US 2012/0283829 A1     Nov. 8, 2012

Related U.S. Application Data

(60) Provisional application No. 61/295,202, filed on Jan. 15, 2010.

(51) Int. Cl.
*A61F 2/08* (2006.01)
*A61L 27/36* (2006.01)

(52) U.S. Cl.
CPC ............. *A61F 2/08* (2013.01); *A61L 27/3604* (2013.01); *A61L 27/3645* (2013.01); *A61L 27/3662* (2013.01)

(58) Field of Classification Search
CPC ....... A61F 2/08; A61F 2/0805; A61F 2/0811; A61F 2002/0823; A61F 2002/0847; A61F 2002/0882; A61L 27/3604; A61L 27/3645; A61L 27/3662

USPC .......... 623/13.11, 13.12, 13.13, 13.14, 13.15, 623/13.16, 13.17, 13.18, 13.19, 13.2
See application file for complete search history.

(56) References Cited

U.S. PATENT DOCUMENTS 4,759,765 A * 7/1988 Van Kampen ............. 623/13.14
5,026,398 A * 6/1991 May et al. .................. 623/13.11
(Continued)

FOREIGN PATENT DOCUMENTS

EP           1 013 239 B1     2/2005

OTHER PUBLICATIONS

Amir et al. Harvesting Large Fascia Lata Sheaths: A Rational Approach. Skull Base Surgery. 2000 10(1): 29-34.*
(Continued)

*Primary Examiner* — David Isabella
*Assistant Examiner* — Rokhaya Diop
(74) *Attorney, Agent, or Firm* — David L. King

(57) ABSTRACT

Cruciate ligament substitutes are formed using fan-folded iliotibial band grafts of fascia lata. Devices of making the same and methods of making and using the same are described herein. The thick fan-folded grafts of fascia lata cruciate ligament substitutes disclosed herein are used in a single-loop fashion and have surprisingly exhibited load to failure and stiffness values that compare favorably with conventional grafts, including tibialis anterior, tibialis posterior, peroneus longus, and bone-patellar tendon-bone (BPTB) half-patella specimens, when the harvested iliotibial band grafts of fascia lata avoid portions thicker than 5 mm, or even 3 mm.

4 Claims, 24 Drawing Sheets

(56) References Cited

U.S. PATENT DOCUMENTS

| | | | |
|---|---|---|---|
| 5,098,508 A | | 3/1992 | Mattil |
| 2004/0243235 A1* | | 12/2004 | Goh et al. .................. 623/13.17 |
| 2004/0267362 A1 | | 12/2004 | Hwang et al. |
| 2009/0222052 A1 | | 9/2009 | Vandewalle |
| 2011/0208305 A1 | | 8/2011 | Malinin et al. |

OTHER PUBLICATIONS

Ellison, et al.; Distal Iliotibial-Band Transfer for Anterolateral Rotator Instability of the Knee. 1979, Journal of Bone Joint Surgery, (1979) vol. 61-A, pp. 330-337.

Noyes, et al.; Biomechanical Analysis of Human Ligament Grafts used in Knee-Ligament Repairs and Reconstructions. (1984), Journal of Bone Joint Surgery, vol. 66, pp. 344-352.

Pearsall, et al.; A Biomechanical Comparison of Three Lower Extremity Tendons for Ligamentous Reconstruction . . . (2003), Journal for Arthroscopic, vol. 19, No. 10 pp. 1091-1096.

Wilson, et al.; A biomechanical Analysis of Matched Bone-Patellar Tendon-Bone and Double-Looped Semitendinosus and Gracilis . . . (1999), Am J Sports Med., vol. 27, pp. 202-207.

Donahue, et al.; A Biomechanical Evaluation of Anterior and Posterior Tibialis Tendons as Suitable Single-Loop Anterior . . . (2002), Journal Arthroscopy, vol. 18, pp. 589-597.

Smolka, et al.; Reconstruction of the palatal aponeurosis with autogenous fascia lata in secondary radical intravelar velo . . . (2008) Int J Oral Maxillofac. Surg. 37: 756-760.

Yamazaki, et al.; Using Fascia Lata to Treat Infective Aortic False Aneurysm; (2005) The Society of Thoracic Surgeons; 79: 1425-1427.

Eisenlohr; Allograft Tissue Sterilization Using Irradiation—What are the Implications for Clinical Performance?; (2007) A Bio-Implants Brief; pp. 1-6.

\* cited by examiner

FAN FOLDED FASCIA LATA FOR CRUCIATE LIGAMENT SUBSTITUTION AND METHOD AND APPARATUS FOR MAKING THE SAME

CROSS-REFERENCE TO RELATED APPLICATIONS

This application claims the benefit of Provisional Application Ser. No. 61/295,202 filed Jan. 15, 2010, which is herein incorporated by reference in its entirety.

FIELD OF THE INVENTION

The present invention is generally directed toward fan-folded fascia lata for cruciate ligament substitution, devices for making the same, and methods of using the same.

BACKGROUND OF THE INVENTION

Damaged and ruptured cruciate ligaments of the knee (anterior and posterior) can be corrected with surgical treatment. If left untreated, chronic pain, instability, laxity and degenerative joint changes are the result. The anterior cruciate ligament ("ACL") and the posterior cruciate ligament ("PCL") are frequently subject to traumatic injury, frequently related to sports activities. Because of the mode of inflicted trauma these injuries occur most frequently in younger people.

Ligament reconstruction, but not repair, results in the alleviation of pain, reduction in the knee effusion, improved stability and return to normal physical activity. The method of surgical intervention typically employed has been the replacement of the torn ligament with patella tendon of the patient attached to pieces of bone from the tibia and the patella. These are placed in tunnels drilled in the tibia and the femur. The procedure is an effective one, but it is associated with a relatively high morbidity rate and increased operation duration to harvest and prepare autograft. In addition, in case of failure, new autografts are no longer available. For these reasons, allografts and xenografts have been used in lieu of autografts. Xenografts have not met with much success, but allografts provide a number of anatomic structures, which can be employed as ACL and PCL substitutes. Since partial and complete tears of the ACL are very common, the demand for ACL substitute allografts is great. It is estimated that in the US over 100,000 ACL and PCL reconstructions are performed annually.

An allograft which anatomically matches the successfully used autografts is the bone-patellar tendon-bone construct. However, not only is the availability of these allografts limited, but there is also a problem with length. These include Achilles tendons, tibialis anterior and tibialis posterior tendons, tendons of hamstring muscles and others.

SUMMARY

Cruciate ligament substitutes formed using fan-folded fascia lata grafts are described herein. Devices of making the same and methods of making and using the same are also described herein. Unless otherwise defined, all technical terms used herein have the same meaning as commonly understood by one of ordinary skill in the art to which this invention belongs.

Accordingly, described herein is a a cruciate ligament substitute including a fan-folded fascia lata sheet, including a fascia lata sheet having longitudinally-oriented first and second edges opposite one another, and laterally-oriented first and second ends opposite one another, the fan-folded fascia lata sheet including at least three longitudinally oriented folds defining at least four layers of fascia lata; and at least one anchoring member anchoring a portion of the fascia lata sheet in a fan-folded orientation. The at least one anchoring member can include an anchoring member anchoring the fan-folded fascia lata sheet proximate the first or second end of said fan-folded fascia late sheet. The at least one anchoring member can further include at least one lateral anchoring member anchoring the fan-folded fascia lata sheet intermediate the first and second ends. The at least one anchoring member can include a first anchoring member anchoring the fan-folded fascia lata sheet proximate the first end and a second anchoring member anchoring the fan-folded fascia lata sheet proximate a second end of the fan-folded fascia lata sheet. The at least one anchoring member can be, e.g., a suture, a removable anchoring member, or a combination thereof. The at least one anchoring member can include an anchoring member anchoring the first end to the second end. The cruciate ligament substitute can be an anterior cruciate ligament substitute or a posterior cruciate ligament substitute. In one embodiment, the at least one anchoring member passes through each of the at least four layers of fascia lata. The fan-folded fascia lata sheet can include at least four longitudinally oriented folds defining at least five layers of fascia lata. For example, the fan-folded fascia lata sheet can include at least five longitudinally oriented folds defining at least six layers of fascia lata. The cruciate ligament substitute can further include a lateral fold at a middle portion of the fan-folded fascia lata sheet.

Also described herein is an apparatus for handling a fascia lata, including first and second removable anchoring members, each of the removable anchoring members including: a base having a first surface, a post extending from the first surface, and a fastener for removable attachment to the base, the fastener including a cavity for receiving the post when the fastener is attached to the base; and a frame having a first end and a second end at opposite ends of said frame, the first end including a first cavity for receiving the first removable anchoring member and the second end including a second cavity for receiving the second removable anchoring member. The frame can include a folding plate, the folding plate including the first and second cavities and a folding surface extending between the first and second cavities, the post of the first removable anchoring member extending above the folding surface when the base of the first removable anchoring member is placed in the first cavity, and the post of the second removable anchoring member extending above the folding surface when the base of the second removable anchoring member is placed in the second cavity. The frame can include a support structure base that includes a first holding portion and a second holding portion connected at opposite ends of a base separating member, the first holding portion including the first cavity and the second holding portion including the second cavity. The apparatus can further include a support rack for supporting material extending between the first and second removable anchor members, the support structure base maintaining a support surface of the support rack at a level of the first surfaces. The support rack can have a generally rectangular shape with a longitudinal axis extending from the first holding portion to the second holding portion, the support rack being foldable along a longitudinal fold line, the fold line arranged such that first and second longitudinal edges of the support rack overlap when the support rack is in a folded position. The apparatus can further include at least two aligned suture windows along the first and second longitudinal edges, or at least one suture window extending across the longitudinal fold line, or both. In one embodiment, the apparatus further includes a support structure top including a first capping portion and a second capping portion connected at opposite ends of a top separating member, the first capping portion including a first fastener cavity dimensioned to receive the fastener of the first removable anchoring member and the second capping portion including a second fastener cavity dimensioned to receive the fastener of the second removable anchoring member.

Further described herein is a method of fan-folding a fascia lata. The method includes: providing a fascia lata sheet having longitudinally-oriented first and second edges opposite one another and laterally-oriented first and second ends opposite one another; providing an apparatus including first and second removable anchoring members, each of the removable anchoring members including a base having a first surface, a post extending from the first surface, and a fastener for removable attachment to the base, the fastener including a cavity for receiving the post when the fastener is attached to the base; and a frame having a first end and a second end at opposite ends of the frame, the first end including a first cavity for receiving the first removable anchoring member and the second end including a second cavity for receiving the second removable anchoring member; attaching a first portion of the fascia lata sheet proximate the first end and the first edge to a post extending from the first removable anchoring member; and attaching a second portion of the fascia lata sheet proximate the second end and the first edge to a post extending from the second removable anchoring member. The method can further include folding the fascia lata to form a longitudinal fold line, the facia lata including an anchored portion between the first edge and the longitudinal fold line and a free portion between the longitudinal fold line and the second edge; attaching a portion of the free portion proximate the first end to the post extending from the first removable anchoring member; and attaching a portion of the free portion proximate the second end to the post extending from the second removable anchoring member. In this embodiment, the method can further include repeating the steps of folding the fascia lata to form a longitudinal fold line, attaching a portion of the free portion proximate the first end to the post extending from the first removable anchoring member, and attaching a portion of the free portion proximate the second end to the post extending from the second removable anchoring member in order to form a fan-folded fascia lata sheet including at least four (e.g., five layers). The method can further include fastening a fastener of the first removable anchoring member to the base of the first removable anchoring member; or fastening a fastener of the second removable anchoring member to the base of the second removable anchoring member; or both. In one embodiment, a frame of the apparatus further includes a folding plate that includes first and second cavities and a folding surface extending between the first and second cavities, the post of the first removable anchoring member extending above the folding surface when the base of the first removable anchoring member is placed in the first cavity, and the post of the second removable anchoring member extending above the folding surface when the base of the second removable anchoring member is placed in the second cavity.

Still further described herein is a method of producing a cruciate ligament substitute. The method includes providing a facia lata sheet having longitudinally-oriented first and second edges opposite one another, and laterally-oriented first and second ends opposite one another, the fascia lata sheet being secured in a fan-folded orientation with at least one removable anchoring member; and securing the fan-folded fascia lata in a fan-folded orientation with at least one permanent anchoring member. This method can further include securing a first end and a second end of the fan-folded facia lata together using at least one permanent anchoring member to form a single-loop facia lata substitute. The at least one removable anchoring member can include a post for anchoring the fascia lata sheet.

Also described herein is a method of producing a cruciate ligament substitute including providing a facia lata sheet having longitudinally-oriented first and second edges opposite one another, and laterally-oriented first and second ends opposite one another; fan-folding the facia lata sheet; and securing the facia lata sheet in a fan-folded orientation with at least one removable anchoring member.

In another embodiment, a folding template includes a generally rectangular folding rack including a first longitudinal edge and a second longitudinal edge opposite the first longitudinal edge, the folding rack including at least three spaced-apart, longitudinally-oriented fold lines for folding the folding rack in a fan-folded orientation; and at least one set of aligned suture windows along at least one longitudinally-oriented fold line, at least one longitudinal edge, or both of the folding rack when the folding rack is in the fan-folded orientation. The folding template can include at least one set of aligned suture windows along each of two longitudinally-oriented fold lines of the folding rack that are adjacent one another when the folding rack is in the fan-folded orientation. A method of fan-folding a fascia lata can include providing a fascia lata sheet having longitudinally-oriented first and second edges opposite one another and laterally-oriented first and second ends opposite one another.

Although ligament substitutes, apparatuses, and methods similar or equivalent to those described herein can be used in the practice or testing of the present invention, suitable ligament substitutes, apparatuses, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

A fuller understanding of the present invention and the features and benefits thereof will be obtained upon review of the following detailed description together with the accompanying drawings, in which.

DETAILED DESCRIPTION

Described herein are cruciate ligament substitutes formed using fan-folded fascia lata grafts, as well as devices of making the same and methods of making and using the same. The fan-folded fascia lata cruciate ligament substitutes disclosed herein are used in a single-loop fashion and have surprisingly exhibited load to failure and stiffness values that compare favorably with conventional grafts, including tibialis anterior, tibialis posterior, peroneus longus, and bone-patellar tendon-bone (BPTB) half-patella specimens.

Figure 15:
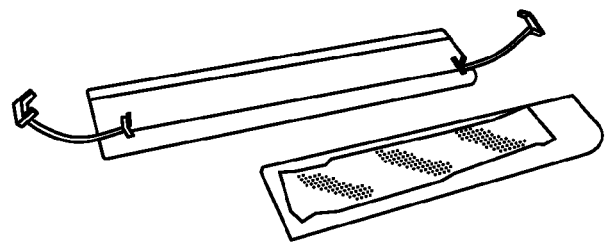
FIG. 15 is a picture showing a generally rectangular fascia lata sheet and an apparatus for handling a fascia lata sheet according to an embodiment of the invention.
Figure 29:
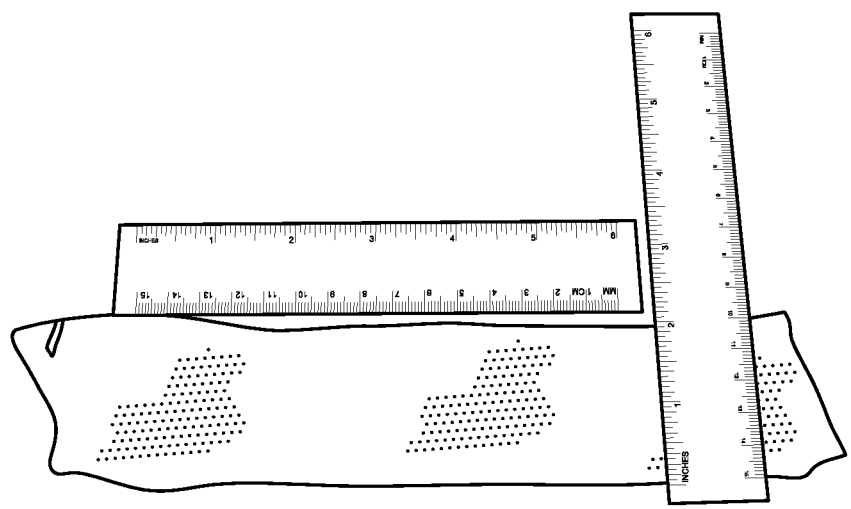
FIG. 29 is a picture of a sheet of fresh-frozen fascia lata harvested from the mid-thigh region where tissue consistency is even.

In one embodiment, the invention is drawn to a cruciate ligament substitute formed from a fan-folded fascia lata sheet. As shown in FIGS. 15 and 29, the fascia lata sheet can be generally rectangular, and can include longitudinally-oriented first and second edges opposite one another and laterally-oriented first and second ends opposite one another. The fan-folded fascia lata sheet can include at least three longitudinally oriented folds defining at least four layers of fascia lata.

The cruciate ligament substitute can also include at least one anchoring member anchoring a portion of the fascia lata sheet in a fan-folded orientation. The anchoring member can anchor the fascia lata sheet by passing through each of the at least four layers of fascia lata. For example, the anchoring member can pass through a series of aligned holes in each of the fascia lata layers. The cruciate ligament substitute can be an anterior cruciate ligament substitute or a posterior cruciate ligament substitute.

As used herein, "fan-folded" is used to refer to a sheet that is folded along a series of parallel fold lines, where adjacent folds are folded in opposite directions. The parallel fold lines can be spaced at regular or irregular intervals. In general, the fold lines will be spaced at regular intervals.

As used herein, "generally rectangular" refers to a sheet having a shape resembling a rectangle in that the shape is two major longitudinal edges and laterally extending end portions. The shape of the end portions is not critical and each end portion may include one or more major edges. A sheet can be generally rectangular and include some minor edges or even have a curved end portion. For example, the fascia lata in FIG. 29 is generally rectangular even though it includes some minor sides proximate the first and second end.

The generally rectangular fascia lata can be at least 15×3 cm in size in order to be used in the cruciate ligament substitutes discloses herein. The fascia lata sheet can be at least 17×4 cm or at least 20×5 cm.

The anchoring members can be used to anchor the fan-folded fascia lata sheet proximate the first or second end of the fan-folded fascia lata sheet. For example, FIGS. 17-23 show a post of a removable anchoring member anchoring the fan-folded fascia lata sheet proximate the first and second ends of a fascia lata sheet.

Figure 31:
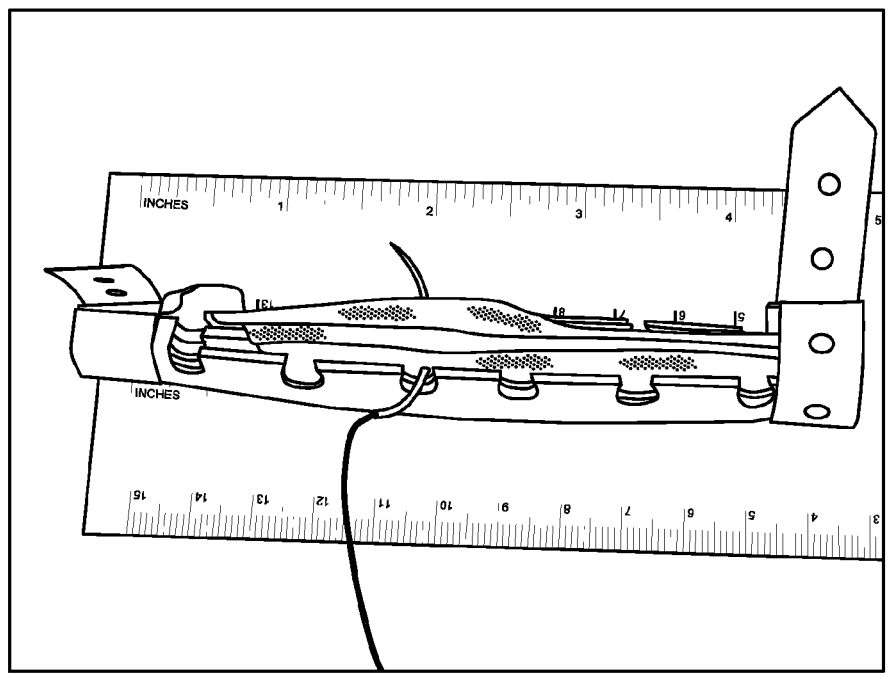
FIG. 31 is a picture showing sutures being added to an edge of a fan-folded and compressed fascia lata sheet through suture windows in the folding template.
Figure 37:
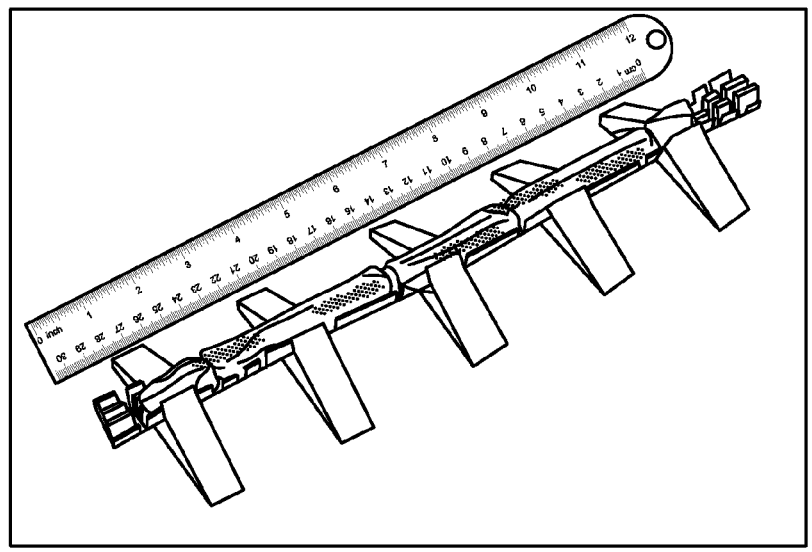
FIG. 37 is a picture of a fan-folded fascia lata sheet held in a folding template where sutures have been added through the suture windows in the folding template.
Figure 38:
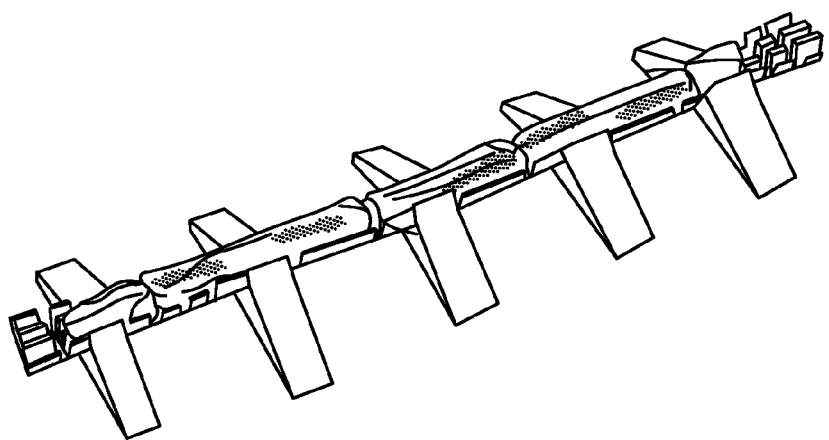
FIG. 38 is a series of views of a base and a fastener of a removable anchoring member according to an embodiment of the invention.

The anchoring members can also be used to anchor the fan-folded fascia lata sheet intermediate the first and second ends. For example, FIGS. 37 and 38 show permanent anchoring members, such as sutures, anchoring the fan-folded fascia lata sheet. In addition, FIG. 31 shows a suture being placed in the fan-folded fascia lata sheet.

The anchoring member can be removable or permanent. Examples of permanent anchoring members include, but are not limited to, sutures, staples and other relatively permanent surgical anchors. As used herein, "permanent" refers to anchoring members that are not intended to be removed. Permanent anchoring members include both non-absorbable sutures and absorbable sutures. Non-absorbable sutures include, but are not limited to, nylon and polypropylene. Absorbable sutures include, but are not limited to, sutures based on polyglycolic acid, polylactic acid and polydioxanone. Absorbable sutures can be designed to be stable within the body for at least two weeks and completely absorbed by the body after a period of at least 50 days. Exemplary sutures include those sold under the trade name VICRYL, an absorbable, polyglycolic, suture available from Ethicon, Inc.

Figure 39:
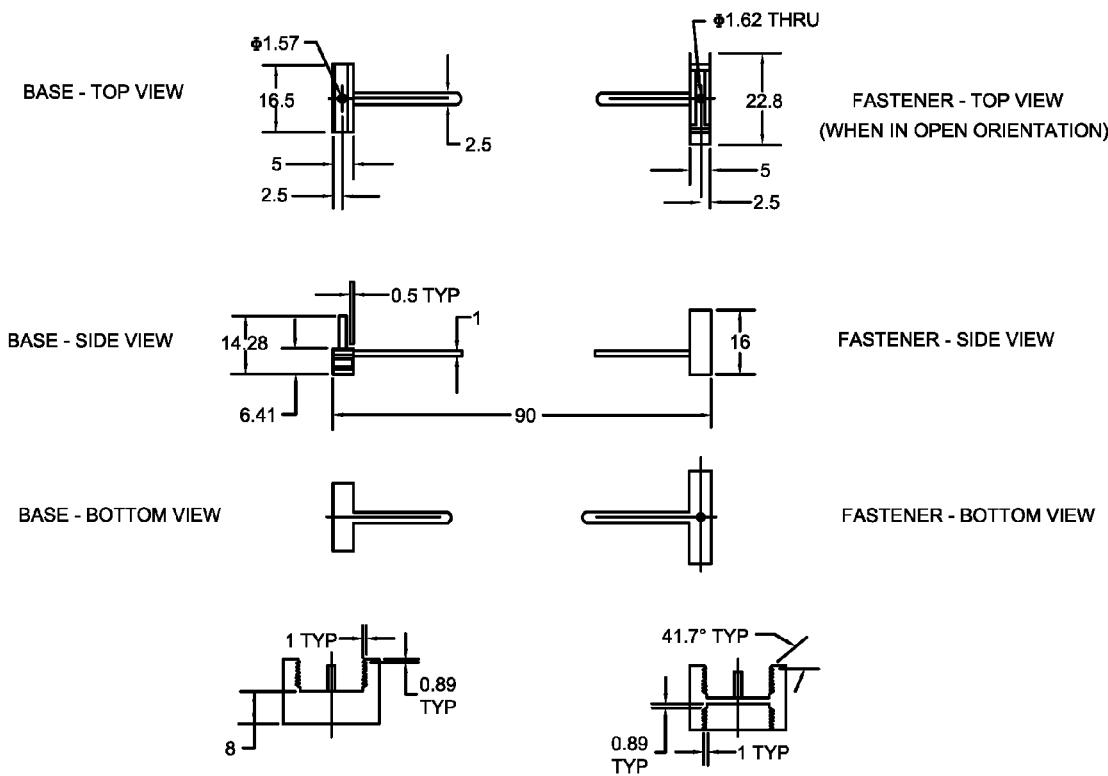
FIG. 39 is a series of views of the base and fastener of a removable anchoring member according to an embodiment of the invention.

Examples of removable anchoring members include anchoring members that are made for easy removal and are intended to be removed prior to implanting the cruciate ligament substitute. Removable anchoring members include, but are not limited to, the clip-type designs shown in FIGS. 15-27. FIG. 39 includes multiple views of the base and fastener of a removable anchoring member according to an embodiment of the invention.

The cruciate ligament substitute can include an anchoring member attaching portions proximate the first end and the second end to form a single-loop, fan-folded fascia lata sheet. The anchoring member attaching the first and second ends can be a permanent anchoring member. The simple-loop, fan-folded fascia lata sheet can include a lateral fold in a middle portion of the cruciate ligament substitute. As used herein, "middle portion" is used to refer to the middle fifty percent of the cruciate ligament substitute as measured along the length of the fan-folded fascia lata sheet.

The fan-folded fascia lata sheet can include at least four longitudinally oriented folds defining at least five layers of fascia lata. Similarly, the fan-folded fascia lata sheet can include at least five longitudinally oriented folds defining at least six layers of fascia lata.

Figure 24:
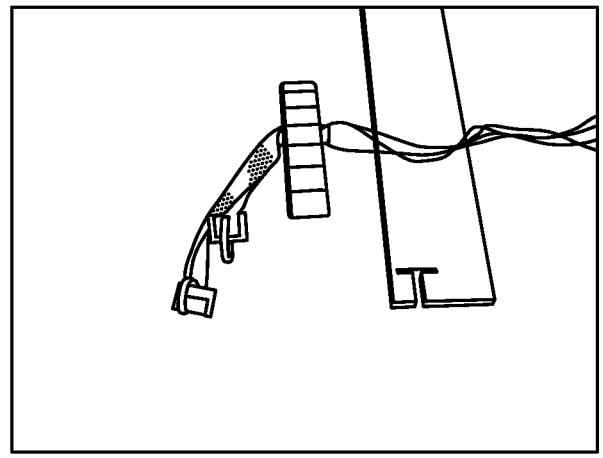
FIG. 24 is a picture showing the diameter of a single-loop, fan-folded facia lata being measured using a tendon sizer.
Figure 25:
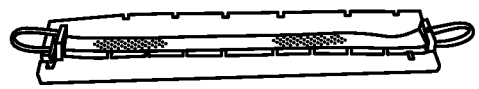
FIG. 25 is a picture showing a front view of a fan-folded fascia lata sheet anchored to removable anchoring members that are in the fastened position and a folding plate with first and second cavities for receiving the removable anchoring members according to an embodiment of the invention.

It has been demonstrated that single-loop, fan-folded fascia lata sheets can exhibit mechanical properties that compare favorably with existing cruciate ligament grafts. In general, single-loop, fan-folded fascia lata sheets determined to have a diameter of at least 6 mm using a tendon sizer, as shown in FIG. 24, exhibited desirable mechanical properties. In some instances, the single-loop, fan-folded fascia lata sheet can have a diameter of at least 7 mm using a tendon sizer, or at least 8 mm using a tendon sizer. The single-loop, fan-folded fascia lata sheet can have a diameter of no more than 12 mm using a tendon sizer, or no more than 11 mm using a tendon sizer, or no more than 10 mm using a tendon sizer, or no more than 9 mm using a tendon sizer. As shown in FIG. 24, the diameter of a single-loop, fan-folded fascia lata sheet can be determined using a tendon sizer by looping a thick suturing thread through the looped, fan-folded fascia lata sheet and attempting to pull the looped, fan-folded fascia lata sheet through an opening in the tendon sizer.

A potential advantage in the single-loop, fan-folded fascia lata constructs disclosed herein is a potentially decreased time for biologic incorporation. Since allograft tissues incorporate from the periphery, it is believed that the fan-folded graft construct with numerous layers and a large exposed surface area will incorporate cellular material from the synovial fluid faster and more uniformly than conventional solid tubular grafts, such as tibialis tendons.

Figure 22:
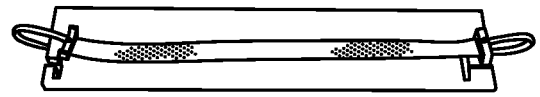
FIG. 22 is a picture showing a front view of a fan-folded fascia late sheet anchored to removable anchoring members that are in the fastened position and a folding plate with first and second cavities for receiving the removable anchoring members according to an embodiment of the invention.

The invention is also drawn to an apparatus for handling a fascia lata sheet. The apparatus can include a first and a second removable anchoring member. Each of the removable anchoring members can include a base having a first surface, a post extending from the first surface, and a fastener for removable attachment from the base. The fastener can include a cavity for receiving the post when the fastener is attached to the base. As shown in FIG. 22, where the posts pass through the fastener, the cavity can be a hole passing from an interior surface of the fastener to an exterior surface of the fastener. However, the cavity can have any shape so long as it prevents a facia lata layer anchored to the post from falling off the post when the fastener is fastened to the base.

The post can extend orthogonally from the first surface of the base. As used herein, an object extends "orthogonally," if it extends in a direction that is generally normal to the surface from which it extends. However, "orthogonally" is also intended to include minor deviations from the normal vector, such as a deviation of 15° or less, or 10° or less, or 5° or less.

Figure 23:
FIG. 23 is a picture showing a front view of a fan-folded fascia lata sheet anchored to removable anchoring members that are in the fastened position and a folding plate with first and second cavities according to an embodiment of the invention.
Figure 26:
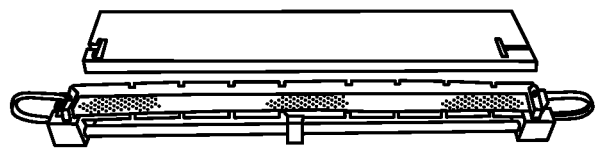
FIG. 26 is a picture showing a fan-folded fascia late anchored to removable anchoring members that is resting in a support structure according to the invention.

As shown in FIGS. 22, 23 and 26, the apparatus can include a frame having a first end and a second end at opposite ends of the frame. The first end of the frame can include a first cavity for receiving the first removable anchoring member and the second end of the frame can include a second cavity for receiving the second removable anchoring member.

Figure 27:
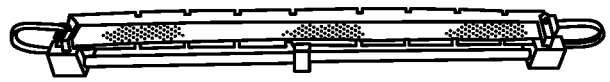
FIG. 27 is a picture showing a fan-folded fascia lata anchored to removable anchoring members that is resting in a support structure according to the invention.
Figure 28:
FIG. 28 is a picture showing a fan-folded fascia lata anchored to removable anchoring members that is resting in a support structure according to the invention.

The Figures show two frames that are useful for the facia lata handling apparatus. The frames include a folding plate, which is shown in FIGS. 15-23, and a support structure, which is shown in FIGS. 26-28. The folding plate is used to hold the removable anchoring members at a fixed distance from one another. The folding plate allows a fascia lata sheet of an acceptable length to be anchored in a fan-folded orientation using the posts of the removable anchoring members.

Once the fascia lata is fan-folded and anchored using the removable anchoring members, the fan-folded fascia lata can be removed from the folding plate and placed in the support structure. The support structure can include a base and a top portion having cavities for receiving the removable anchoring member bases and fasteners, respectively. The support structure is used for transport and storage of the removably anchored fan-folded fascia lata.

The support structure is designed such that there are matching sets of suture windows. The suture windows enable the implanting surgeon or a medical professional supporting the surgeon to add permanently anchors, such as sutures, to anchor the fascia lata in a fan-folded, single loop orientation prior to implantation.

As shown in FIGS. 15-23, the frame can include a folding plate. The folding plate can include the first and second cavities and a folding surface extending between the first and second cavities. The post of the first removable anchoring member can extend above the folding surface when the base of the first removable anchoring member is placed in the first cavity. Similarly, the post of the second removable anchoring member can extend above the folding surface when the base of the second removable anchoring member is placed in the second cavity.

As shown in FIGS. 26-28, the frame can also include a support structure base. The support structure base can include a first holding portion and a second holding portion connected at opposite ends of a base separating member. The first holding portion can include the first cavity and the second holding portion can include the second cavity.

The support structure can also include a support rack for supporting the fan-folded fascia lata extending between the first and second removable anchor members. The support structure base can be designed to maintain a support surface of the support rack at a level of the first surfaces of the removable anchor members.

The support rack can be a sheet having a generally rectangular shape with a longitudinal axis extending from the first holding portion to the second holding portion. The support rack can be foldable along a longitudinal fold line that is arranged such that first and second longitudinal edges of the support rack overlap when the support rack is in a folded position.

The support rack can include at least one set of matching suture windows along the first and second longitudinal edges, or the support rack can include at least at least one suture window extending across the longitudinal fold line, or the support rack can include both.

As used herein, "suture window" refers to a cut out from a sheet, such as a support rack, that enables a medical professional to suture a material supported in the sheet without simultaneously attaching the material to the sheet. For example, as shown in. FIG. 31, suture windows enable introduction of sutures to a fan-folded fascia lata sheet held in a folding template in a manner that the fan-folded fascia lata sheet can be removed from the folding template with the suture intact.

As shown in FIG. 28, the support structure can also include a support structure top. The support structure top can include a first capping portion and a second capping portion connected at opposite ends of a top separating member. The first capping portion can include a first fastener cavity dimensioned to receive the fastener of the first removable anchoring member and the second capping portion can include a second fastener cavity dimensioned to receive the fastener of the second removable anchoring member.

As shown in FIGS. 26-28, the support structure base and top can also include support rack stabilizing components between the holding portions, between the capping portions or both. The rack stabilizing components can be attached to the applicable separating member. The rack stabilizing component(s) can be dimensioned to maintain a support surface of the support rack at a level of the first surfaces of the removable anchor members.

Figure 1:
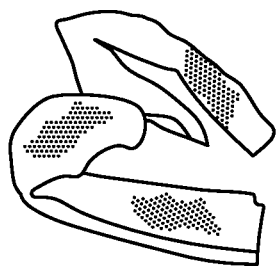
FIG. 1 is a picture showing a piece of fascia lata after harvesting.
Figure 2:
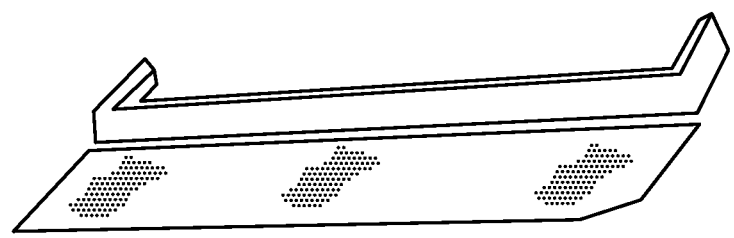
FIG. 2 is a picture showing a table arranged for performing a method according to the invention.
Figure 3:
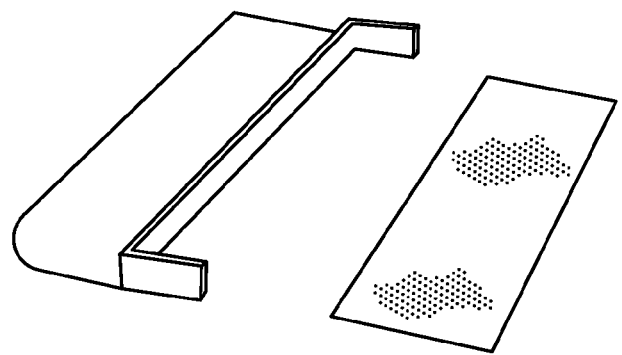
FIG. 3 is a picture showing a facia lata sheet being prepared for trimming to a generally-rectangular shape.
Figure 4:
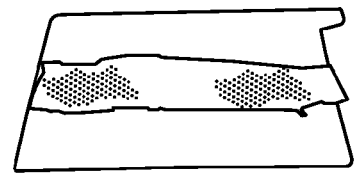
FIG. 4 is a picture showing a facia lata sheet ready for trimming to a generally-rectangular shape.
Figure 5:
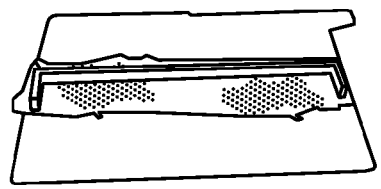
FIG. 5 is a picture showing a facia lata and a straight edge-type guide used to assist with cutting of the fascia lata sheet.
Figure 6:
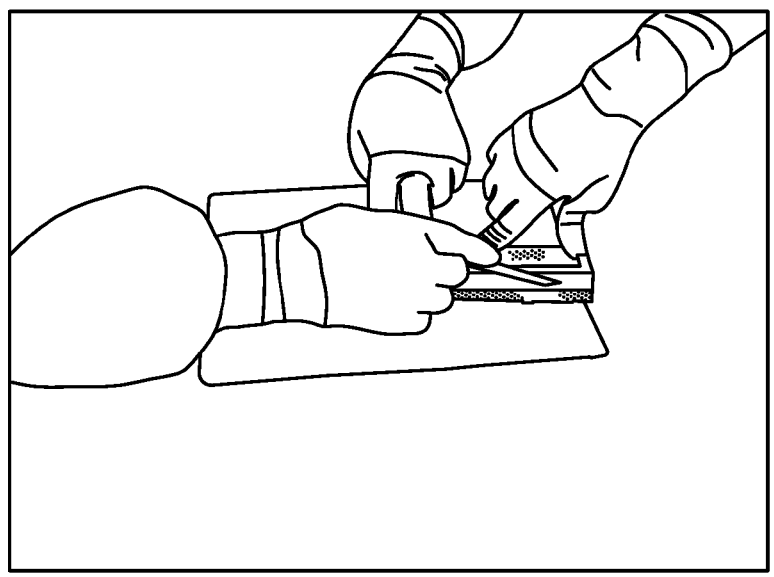
FIG. 6 is a picture showing the fascia lata being cut using a scalpel and a straight edge-type guide.
Figure 7:
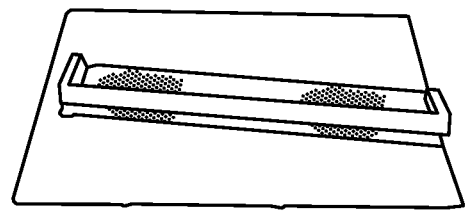
FIG. 7 is a picture showing a piece of the fascia lata sheet that has been removed.
Figure 8:
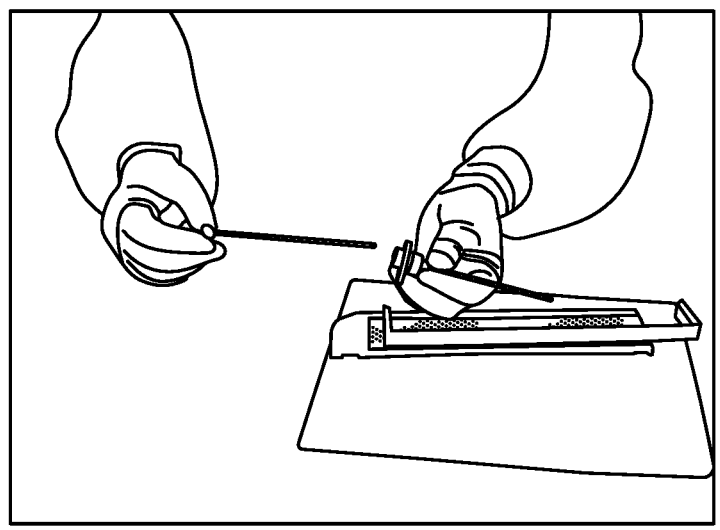
FIG. 8 is a picture showing preparations of a surgical awl for making holes in a fascia lata sheet.
Figure 9:
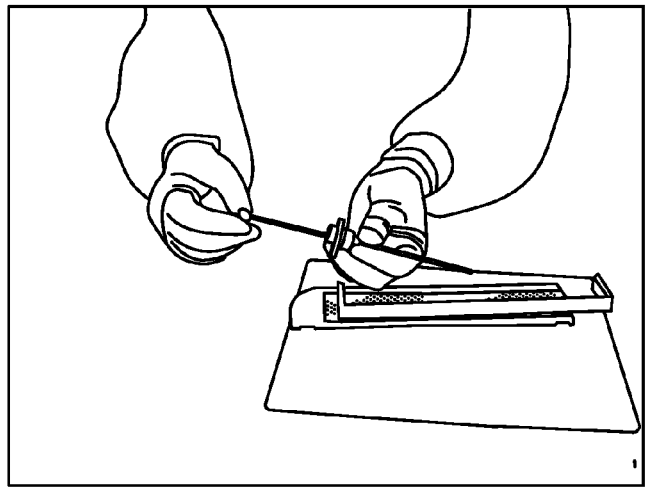
FIG. 9 is a picture showing preparations of a surgical awl for making holes in the fascia lata sheet.
Figure 10:
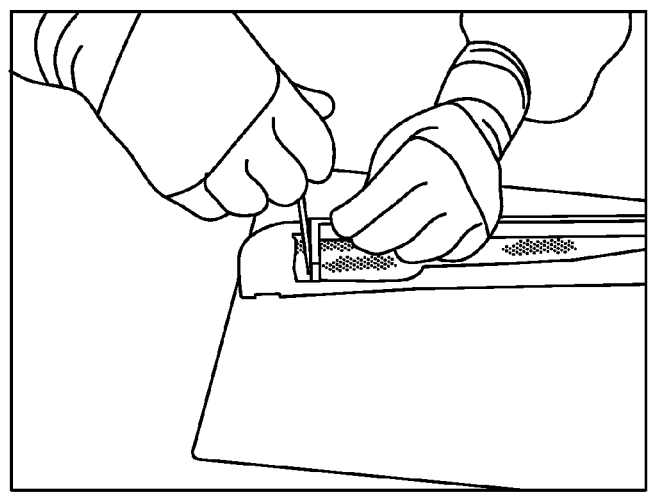
FIG. 10 is a picture showing a surgical awl being used to punch a hole in the fascia lata sheet proximate an end of the fascia lata sheet.
Figure 11:
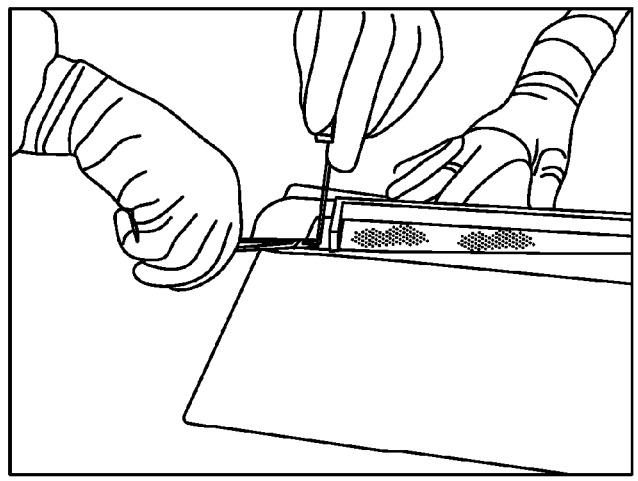
FIG. 11 is a picture showing a surgical awl punching a hole in the fascia lata sheet proximate an end of the fascia lata sheet.
Figure 12:
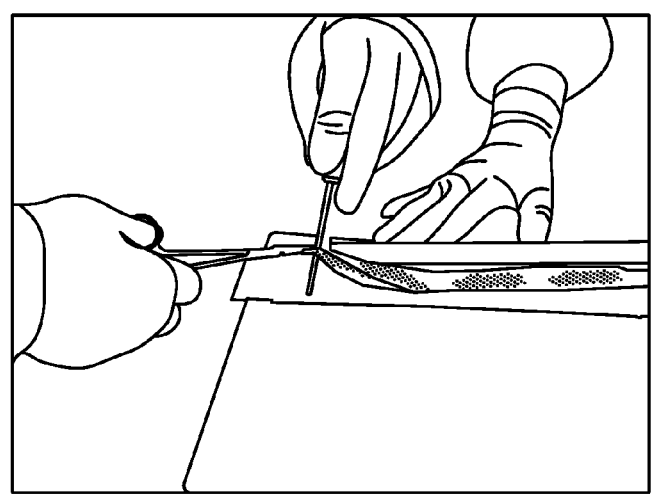
FIG. 12 is a picture showing the surgical awl passing through the fascia lata sheet.
Figure 13:
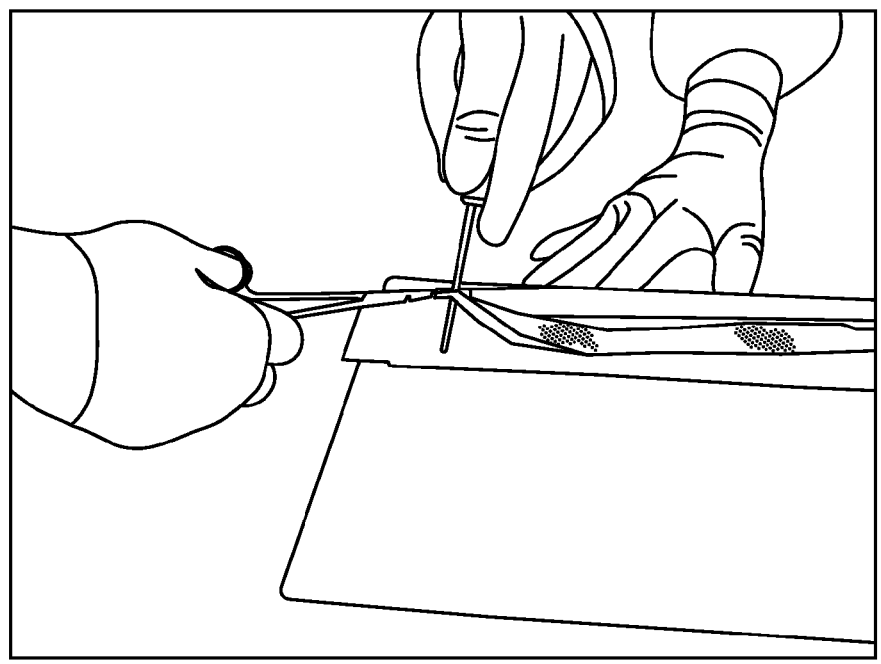
FIG. 13 is a picture showing the surgical awl being removed from the hole formed in the fascia lata sheet.
Figure 14:
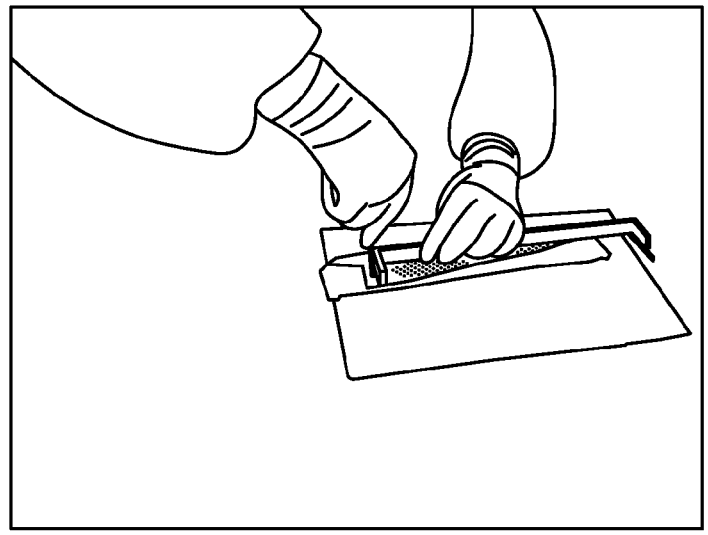
FIG. 14 is a picture of a surgical awl being used to make a hole in a fascia lata sheet.

In another embodiment, the invention is drawn to a method of fan-folding a fascia lata as shown in FIGS. 1-28. The method can include providing a fascia lata sheet having longitudinally-oriented first and second edges opposite one another and laterally-oriented first and second ends opposite one another. A freshly harvested fascia lata is shown in FIG. 1. FIGS. 2-14 show the fascia lata being cut into a generally rectangular shape having longitudinally-oriented first and second edges.

In addition, FIGS. 8-14 show the use of a surgical awl for pre-punching a series of holes proximate the first and second ends of the fascia lata sheet. The holes can be spaced so that the layers of fascia lata are the desired width once the fascia lata is fan-folded.

The method can include providing the apparatus for handling a fascia lata described above, such as the apparatus as shown in FIG. 15. A first portion of the fascia lata sheet proximate the first end and the first edge can be attached to a post extending from the first removable anchoring member. Similarly, a second portion of the fascia lata sheet proximate the second end and the first edge can be attached to a post extending from the second removable anchoring member. Where holes are pre-formed, using a surgical awl or similar device, the first portion and the second portion can be attached using the holes closest to the first edge.

Figure 16:
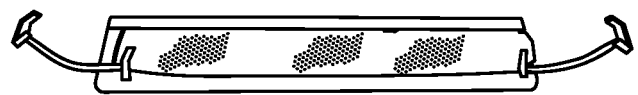
FIG. 16 is a picture showing a generally rectangular facia lata sheet anchored to removable anchoring members according to an embodiment of the invention.
Figure 17:
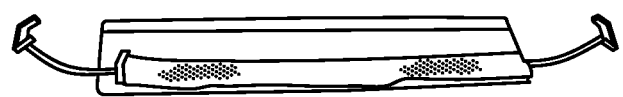
FIG. 17 is a picture of a partially fan-folded fascia lata sheet anchored to removable anchoring members according to an embodiment of the invention.
Figure 18:
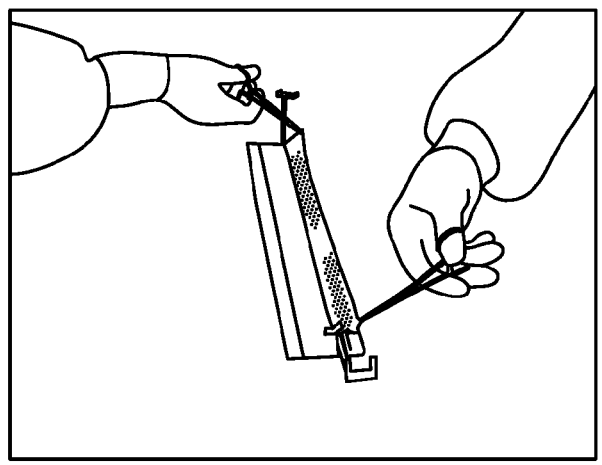
FIG. 18 is a picture of a partially fan-folded fascia lata sheet anchored to removable anchoring members according to an embodiment of the invention.
Figure 19:
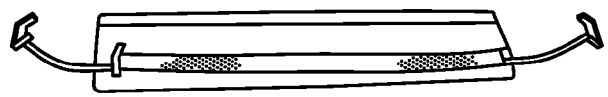
FIG. 19 is a picture of a fan-folded fascia lata sheet resting on a folding plate and anchored to removable anchoring members according to an embodiment of the invention.

The method can also include folding the fascia lata to form a longitudinal fold line. As shown in FIG. 16, the facia lata can include an anchored portion between the first edge and the longitudinal fold line and a free portion between the longitudinal fold line and the second edge. A portion of the free portion proximate the first end can be attached to the post extending from the first removable anchoring member and a portion of the free portion proximate the second end can be attached to the post extending from the second removable anchoring member. The folding and attaching steps can be repeated at least three times to create a fan-folded fascia lata sheet with at least three longitudinal folds and at least four layers. Similarly, the folding and attaching steps can be repeated to produce at least four longitudinal folds and at least five layers, or at least five longitudinal folds and at least six layers.

Figure 20:
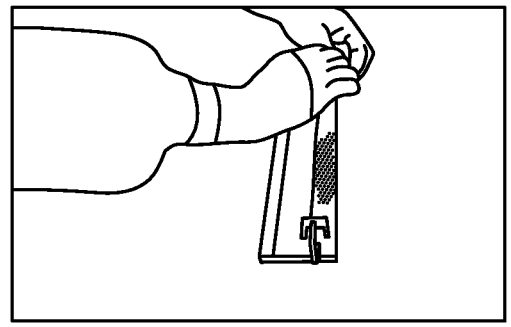
FIG. 20 is a picture showing an end view of a fan-folded fascia lata sheet anchored to removable anchoring members that are in the fastened position.
Figure 21:
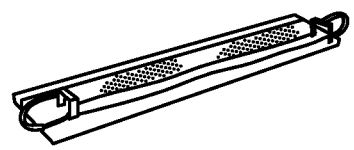
FIG. 21 is a picture showing a perspective view of a fan-folded fascia lata sheet anchored to removable anchoring members that are in the fastened position.

As shown in FIGS. 20-21, the method can also include fastening a fastener of the first removable anchoring member to the base of the first removable anchoring member; fastening a fastener of the second removable anchoring member to the base of the second removable anchoring member; or both. The method can also include transferring the removably anchored fan-folded fascia lata from the folding plate to the support structure. Once in the support structure, the fan-folded fascia lata can be stored, preferably frozen, until such time as the fan-folded fascia lata is ready to be implanted.

Prior to implanting the fan-folded fascia lata, permanent anchors, such as polyglycolic acid-based sutures, can be introduced to anchor the fan-folded fascia lata. Once the permanent anchors are introduced, the fan-folded fascia lata can be removed from the support structure and maintain a fan-folder orientation. The first and second end of the fan-folded fascia lata can then be attached to one another to form a single-loop, fan-folded fascia lata. The single-loop, fan-folded fascia lata can then be implanted using conventional surgical techniques for implanting a cruciate ligament substitute.

In another embodiment, the method of producing a cruciate ligament substitute can include providing a facia lata sheet secured in a fan-folded orientation with at least one removable anchoring member, and securing the fan-folded fascia lata in a fan-folded orientation with at least one permanent anchoring member. The method can also include securing a first end and a second end of the fan-folded facia lata together with at least one permanent anchoring member to form a single-loop facia lata substitute.

In another embodiment, the method of producing a cruciate ligament substitute can include providing a generally-rectangular facia lata sheet, fan-folding the facia lata sheet, and securing the facia lata sheet in a fan-folded orientation with at least one removable anchoring member. The method can also include storing the fascia lata sheet in the fan-folded orientation.

As shown in FIGS. 30, 31 and 34-38, the invention also includes a folding template. The folding template can include a generally rectangular folding rack having a first longitudinal edge and a second longitudinal edge opposite the first longitudinal edge. The folding rack can include at least three spaced-apart, longitudinally-oriented fold lines for folding the folding rack in a fan-folded orientation. The folding rack can also include at least one suture window along at least one longitudinally-oriented fold line, at least one longitudinal edge, or both. The folding rack can include at least two aligned suture windows the folding rack is in the fan-folded orientation. As shown in FIG. 31, the folding template can include at least one set of aligned suture windows along each of two longitudinally-oriented fold lines of the folding rack that are adjacent one another when the folding rack is in the fan-folded orientation.

The function and advantage of these and other embodiments of the present invention will be more fully understood from the examples described below. The following examples are intended to facilitate an understanding of the invention and to illustrate the benefits of the present invention, but are not intended to limit the scope of the invention.

Examples

Methods

Figure 30:
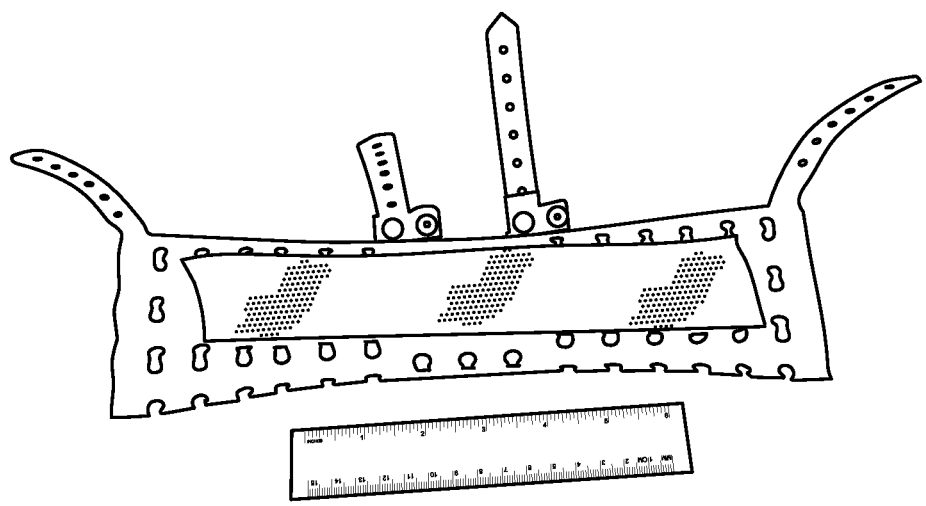
FIG. 30 is a picture of a sheet of fascia lata mounted on a custom cardboard folding template to allow the tissue to be fan-folded folded easily into multiple pleats of the same width.

Eighteen fascia lata specimens were harvested from 11 donors with a mean age of 38 years (range 21 to 56 years). These grafts were harvested from the distal-lateral thigh and were approximately 22 cm in length and 4 cm in width, depending on the donor. All tissue was fresh-frozen after harvesting within 24 hours postmortem. Using a custom template (FIG. 29), the fascia lata specimens were fan-folded to achieve a tubular-like graft that was multiple layers thick (FIG. 30). This fan-folded construct was then secured with several simple sutures along the length of the graft (FIG. 31). The final fascia lata graft was then doubled-over in a single-loop fashion for testing purposes. Prior to testing, each graft was passed through the smallest possible tendon sizer. Of the 14 grafts used in testing, three were 7 mm, five were 8 mm, nine were 9 mm, and one was 10 mm in diameter.

For comparative purposes, four additional donors that had been allocated for research purposes were used to harvest a total of eight tibialis anterior, eight tibialis posterior, and eight peroneus longus, and sixteen BPTB half-patella specimens. The average age of the donors was 46 years (range 25 to 61 years). Each of the soft tissue grafts were atraumatically stripped of any muscle attachment and doubled-over to form a single loop. For tibialis anterior, there was a single 8 mm specimen, six 9 mm specimens, and one 10 mm specimen. For tibialis posterior, there were two 9 mm specimens, five 10 mm specimens, and a single 11 mm specimen. For peroneus longus, there were five 8 mm specimens and two 9 mm specimens. Two half patellar specimens were discarded because of tissue quality and the remaining fourteen specimens were trimmed to a tendon width of 10 mm. The patellar and tibial bone blocks were similarly trimmed to allow fixation by the freeze grips.

After initial harvesting and preparation, all grafts were kept frozen until the day of testing. With a typical harvested sheet, a graft of roughly six layers thick of fascia lata could be fashioned, making the single-loop construct roughly twelve layers thick. With harvested sheet lengths of at least 20 cm, a 10 cm single-loop/double strand graft can easily be created. This would be an adequate length for most clinical scenarios even if cortical fixation devices were to be used. In order to secure the layers of the folded fascia together, suture windows were created in the folding template at regular intervals. This allowed easy placement of regularly-spaced interrupted 3-0 vicryl sutures along the length of the graft to tubularize and secure it. In a clinical setting, the fan-folding and/or suturing of the fascia lata graft can be done at the time of surgery. During harvesting of the fascia lata, it was noted that the thickness of the iliotibial band increased distally in the thigh towards Gerdy's tubercle. However, the tissue consistently at this location was variable and not easily fan-folded into the double-strand construct. As such, the fan-folded fascia lata specimens for use as cruciate ligament substitutions could be harvested from a more central location in the thigh that avoids thicker portions of the iliotibial band near Gerdy's tubercle. In particular, the fascia lata can be harvested to avoid portions that are thicker than 5 mm or the fascia lata can be harvested to avoid portions that are thicker than 3 mm.

Figure 32:
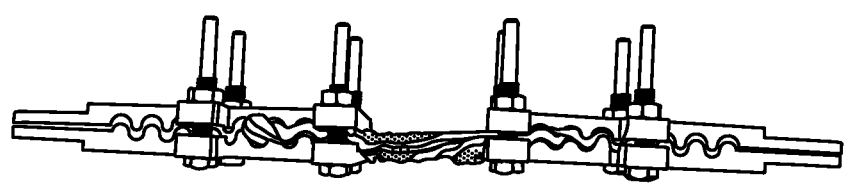
FIG. 32 is a picture of a tissue specimens mounted in serrated clamps with 5 cm of tissue between the clamps.
Figure 33:
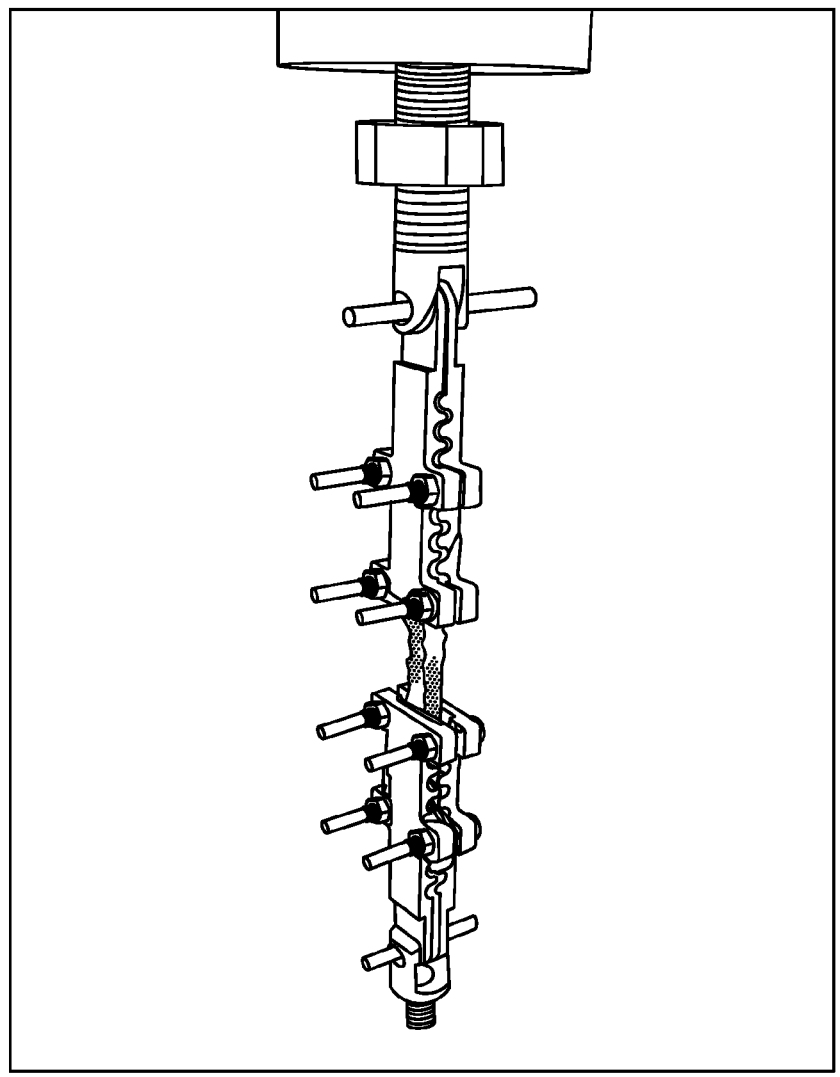
FIG. 33 is a picture of tissue specimens mounted in a tensile testing machine.
Figure 34:
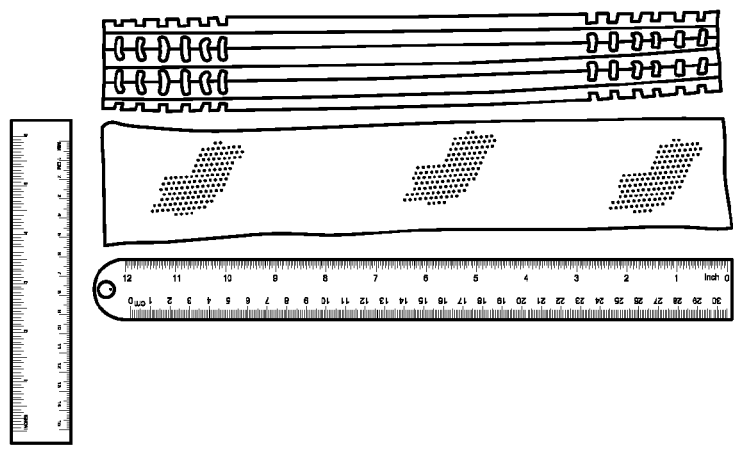
FIG. 34 is a picture of a folding template according to one embodiment of the invention.
Figure 35:
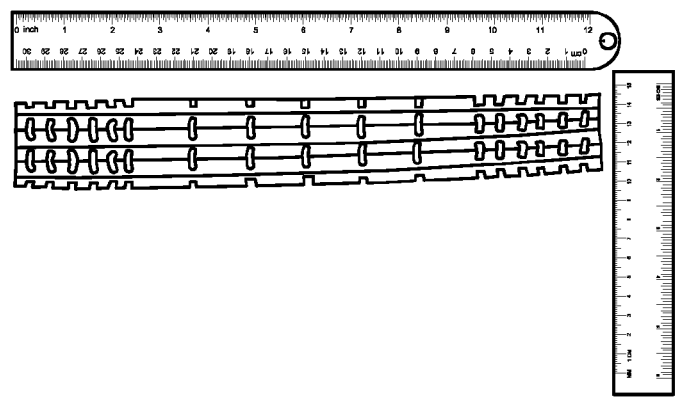
FIG. 35 is a top view of a folding template according to an embodiment of the invention.
Figure 36:
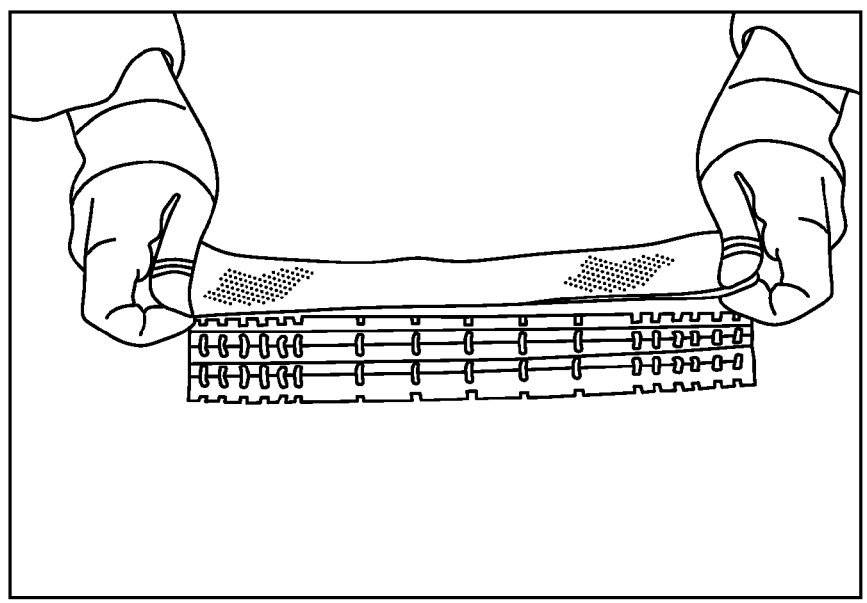
FIG. 36 is a picture of a fascia lata sheet being placed on a folding template according to an embodiment of the invention.

All the soft tissue grafts were in a single-loop configuration and held by serrated metal clamps (FIG. 32) on either end with a distance of 50 mm between the clamps. Both clamps were then frozen in liquid nitrogen for 20 seconds to allow freezing and bonding of the clamped tissue ends to the metal. The intervening 50 mm of tissue between the clamps was left unfrozen. The clamped ends were then mounted on an MTS Mini Bionix 858 testing apparatus and pre-tensioned to 5-15 N to ensure the grafts were taut prior to testing (FIG. 33). The MTS TestStar Station Manager was used to collect information about ultimate tensile strength and stiffness of the grafts (Table 1, below). At this point, the grafts were loaded to failure at a rate proportional to their active length. Since the active length of the soft tissue grafts was 50 mm, elongation was carried out at 5 mm/sec. Values for ultimate tensile strength, stiffness, and mode of failure were recorded. The BPTB grafts were similarly tested with both bone blocks secured by the freeze grips. Statistical analysis consisted of a student's t-test to compare values between fascia lata and the other tested graft types.

TABLE 1

Data for Individual Test Specimens

| Graft Type | Diameter (mm) | Tensile Strength (N) | Stiffness (N/mm) | Graft Type | Diameter (mm) | Tensile Strength (N) | Stiffness (N/mm) |
|---|---|---|---|---|---|---|---|
| Fascia Lata | 7 | 1918.56 | 302.83 | BPTB | 10 | 1015 | 153.4 |
|  |  |  |  | BPTB | 10 | 1454 | 223.1 |
| Fascia Lata | 7 | 1978.82 | 241.69 | BPTB | 10 | 1740 | 240.3 |
|  |  |  |  | BPTB | 10 | 1221 | 290.3 |
| Fascia Lata | 7 | 2022.95 | 231.02 | BPTB | 10 | 1116 | 333.7 |
|  |  |  |  | BPTB | 10 | 870 | 164.5 |
| Fascia Lata | 8 | 2379.57 | 367.60 | BPTB | 10 | 1452 | 276.7 |
|  |  |  |  | BPTB | 10 | 2837 | 336.2 |
| Fascia Lata | 8 | 3160.01 | 398.11 | BPTB | 10 | 1581 | 248.8 |
|  |  |  |  | BPTB | 10 | 1205 | 180.9 |

TABLE 1-continued

Data for Individual Test Specimens

| Graft Type | Diameter (mm) | Tensile Strength (N) | Stiffness (N/mm) | Graft Type | Diameter (mm) | Tensile Strength (N) | Stiffness (N/mm) |
|---|---|---|---|---|---|---|---|
| Fascia Lata | 8 | 2281.51 | 324.86 | BPTB | 10 | 1089 | 256.9 |
| | | | | BPTB | 10 | 1585 | 156.8 |
| Fascia Lata | 8 | 3272.23 | 406.62 | BPTB | 10 | 1697 | 164.3 |
| | | | | BPTB | 10 | 789 | 108.5 |
| Fascia Lata | 8 | 3658.18 | 412.19 | Tib Ant | 8 | 2155 | 237.5 |
| | | | | Tib Ant | 9 | 3965 | 375.0 |
| Fascia Lata | 9 | 4110.24 | 464.32 | Tib Ant | 9 | 1909 | 276.4 |
| | | | | Tib Ant | 9 | 3704 | 498.3 |
| Fascia Lata | 9 | 4323.83 | 536.46 | Tib Ant | 9 | 2268 | 201.1 |
| | | | | Tib Ant | 9 | 3582 | 399.9 |
| Fascia Lata | 9 | 4402.78 | 590.64 | Tib Ant | 9 | 3439 | 378.5 |
| | | | | Tib Ant | 10 | 3075 | 376.3 |
| Fascia Lata | 9 | 2020.68 | 214.54 | Tib Post | 9 | 2304 | 367.0 |
| Fascia Lata | 9 | 4727.42 | 509.70 | Tib Post | 9 | 3352 | 392.8 |
| Fascia Lata | 9 | 4064.68 | 500.52 | Tib Post | 10 | 3740 | 422.0 |
| Fascia Lata | 9 | 3709.99 | 324.14 | Tib Post | 10 | 3158 | 375.8 |
| Fascia Lata | 9 | 2834.70 | 265.20 | Tib Post | 10 | 4205 | 406.0 |
| Fascia Lata | 9 | 3327.07 | 791.27 | Tib Post | 10 | 4471 | 410.2 |
| Fasci Lata | 10 | 4596.53 | 572.16 | Tib Post | 10 | 4691 | 419.2 |
| Per Longus | 8 | 3266 | 292.8 | Tib Post | 11 | 3403 | 347.2 |
| Per Longus | 8 | 3166 | 308.8 | | | | |
| Per Longus | 8 | 3715 | 493.3 | | | | |
| Per Longus | 8 | 3295 | 259.1 | | | | |
| Per Longus | 8 | 3186 | 225.1 | | | | |
| Per Longus | 9 | 1584 | 383.1 | | | | |
| Per Longus | 9 | 3615 | 378.6 | | | | |
| Per Longus | 9 | 2576 | 432.2 | | | | |

RESULTS

The average load to failure for the tested double-strand fan-folded fascia lata grafts was 3266 N (Table 2). This was comparable to the mean values observed for tibialis anterior (3012 N, p=0.52), tibialis posterior (3666 N, p=0.32), and peroneus longus allografts (3050 N, p=0.58) in this study. The fan-folded fascia lata construct performed significantly better than the 10 mm BPTB allograft (1404 N, p<0.001) in this setting. A similar trend was observed for graft stiffness values, with fan-folded fascia lata having the higher mean stiffness (414.10 N/mm). However, this was not statistically significant compared to values for tibialis anterior (343 N/mm; p=0.24), tibialis posterior (392 N/mm; p=0.69), and peroneus longus (347 N/mm; p=0.26). Compared to BPTB (224 N/mm), the fan-folded fascia lata was significantly stiffer (p<0.001).

TABLE 2

Average Data by Graft Type

| Graft | Average Diameter | Ultimate Tensile Strength | Stiffness |
|---|---|---|---|
| Fascia Lata | 8.44 mm | 3266 N (+/− 987 N) | 414 N/mm (+/− 151 N/mm) |
| Tibialis posterior | 9.88 mm | 3666 N (+/− 782 N) P = 0.32 | 392 N/mm (+/− 27 N/mm) P = 0.70 |
| Peroneus longus | 8.38 mm | 3050 N (+/− 684 N) P = 0.58 | 347 N/mm (+/− 91 N/mm) P = 0.26 |
| Tibialis anterior | 9 mm | 3012 N (+/− 794 N) P = 0.53 | 343 N/mm (+/− 97 N/mm) P = 0.24 |
| BPTB | 10 mm | 1403 N (+/− 511 N) P < 0.001 | 224 N/mm (+/− 71 N/mm) P < 0.001 |

*p values are comparing the fascia lata data to each of the other test graft types A separate analysis was performed excluding the three grafts from the fascia lata group which were 7 mm in diameter. The ultimate tensile loads (1919 N, 1979 N, and 2023 N respectively) and stiffness (303 N/mm, 242 N/mm, 231 N/mm) for these 7 mm grafts were markedly lower than the rest of the fan-folded fascia lath specimens. Excluding these 7 mm grafts, the mean ultimate tensile strength of the fan-folded fascia lata specimens increased to 3524 N and the mean stiffness increased to 445 N/mm. However, these values were still not significantly different than the values obtained for the soft-tissue allografts (tibialis and peroneal tendons) tested in this study.

The failure mode for all tested specimens was also recorded. Sixteen of the 18 tested fan-folded fascia lata specimens were purely intrasubstance ruptures whereas only two of 18 failed towards the clamped end. The majority of the failures in the other soft tissue grafts were also intrasubstance ruptures with occasional failures towards the clamps. There were no instances of soft tissue slippage from the freeze clamps. This is in contrast to the BPTB group, where a slight majority of the failures were at the bone-tendon interface with the remainder being intraligamentous ruptures. Again, there were no instances of bone pullout from the clamps.

The values for ultimate tensile strength (3266 N) and stiffness (414 N/mm) for the single-loop, fan-folded fascia lata constructs were comparable to the other soft tissue allografts studied. These numbers improved to 3525 N and 445 N/mm respectively when the smaller 7 mm grafts were excluded from the analysis. The values for the soft tissue grafts in this study (fascia lata, tibialis anterior, tibialis posterior, and peroneus longus) were comparable to similar studies in the literature.

Values for graft stiffness have been reported to range from 210 N/mm for a 10 mm BPTB to 274 N/mm for a 14 mm BPTB graft. The stiffness of the fan-folded fascia lata graft in this study of 414 N/mm greatly exceeds this historical data and is higher than values for the other soft tissue grafts in this and other studies, with ranges from 242 N/mm to 392 N/mm. Based on this data, the single-loop double-stranded, fan-folded fascia lata graft performs at least as well as any other allograft tissue in clinical use today with respect to initial ultimate tensile strength and stiffness.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A method of fan-folding a fascia lata, comprising the steps of:
   harvesting a fascia lata sheet in a length of at least 20 cm from the iliotibial band in a central region of the thigh to avoid portions that are thicker than 5 mm;
   providing a fascia lata sheet having longitudinally-oriented first and second edges opposite one another and laterally-oriented first and second ends opposite one another
   providing an apparatus for handling a fascia lata, having first and second removable anchoring members for removal prior to implanting the fan-folded fascia lata, each of said removable anchoring members comprising a base having a first surface, a post extending from said first surface, and a fastener for removable attachment to said base, wherein said fastener comprises a cavity for receiving said post when said fastener is attached to said base; a frame having a first end and a second end at opposite ends of said frame, wherein said first end comprises a first cavity for receiving said first removable anchoring member and said second end comprises a second cavity for receiving said second removable anchoring member, and wherein said frame has a folding plate, said folding plate including said first and second cavities and a folding surface extending between said first and second cavities, wherein said post of said first removable anchoring member extends above said folding surface when said base of said first removable anchoring member is placed in said first cavity, wherein said post of said second removable anchoring member extends above said folding surface when said base of said second removable anchoring member is placed in said second cavity;
   attaching a first portion of said fascia lata sheet proximate said first end and said first edge to a post extending from said first removable anchoring member;
   attaching a second portion of said fascia lata sheet proximate said second end and said first edge to a post extending from said second removable anchoring member;
   (i) folding said fascia lata to form a longitudinal fold line, wherein said fascia lata comprises an anchored portion between said first edge and said longitudinal fold line and a free portion between the longitudinal fold line and said second edge;
   (ii) attaching a portion of said free portion proximate said first end to said post extending from said first removable anchoring member;
   (iii) attaching a portion of said free portion proximate said second end to said post extending from said second removable anchoring member
   repeating steps (i)-(iii) at least three times, prior to implanting the fan-folded fascia lata permanent anchors are introduced to permanently anchor the fan-folded fascia lata, thereafter the removable fasteners are removed prior to implantation.

2. The method according to claim 1, further comprising: repeating steps (i)-(iii), in order to form a fan-folded fascia lata sheet comprising at least four layers.

3. The method according to claim 1, further comprising: repeating steps (i)-(iii), in order to form a fan-folded fascia lata sheet comprising at least five layers.

4. The method according to claim 1, further comprising:
   fastening a fastener of said first removable anchoring member to said base of said first removable anchoring member; or
   fastening a fastener of said second removable anchoring member to said base of said second removable anchoring member; or
   both.

* * * * *